(12) United States Patent
Khanzhin et al.

(10) Patent No.: US 11,419,884 B2
(45) Date of Patent: Aug. 23, 2022

(54) COMPOSITIONS COMPRISING HMOS, THEIR PRODUCTION AND USE FOR THE PREVENTION AND/OR TREATMENT OF VIRAL AND/OR BACTERIAL INFECTIONS

(71) Applicant: GLYCOM A/S, Hørsholm (DK)

(72) Inventors: Nikolay Khanzhin, Humlebæk (DK); Markus Jondelius Hederos, Trelleborg (SE); Louise Kristine Vigsnæs, København (DK); Bruce McConnell, La Tour de Peilz (CH)

(73) Assignee: GLYCOM A/S, Hørsholm (DK)

( * ) Notice: Subject to any disclaimer, the term of this patent is extended or adjusted under 35 U.S.C. 154(b) by 677 days.

(21) Appl. No.: 16/312,506

(22) PCT Filed: Jun. 23, 2017

(86) PCT No.: PCT/IB2017/053760
§ 371 (c)(1),
(2) Date: Dec. 21, 2018

(87) PCT Pub. No.: WO2017/221208
PCT Pub. Date: Dec. 28, 2017

(65) Prior Publication Data
US 2019/0175631 A1   Jun. 13, 2019

(30) Foreign Application Priority Data

Jun. 24, 2016 (EP) .................................... 16176257
Jun. 24, 2016 (EP) .................................... 16176285
Apr. 19, 2017 (WO) ................. PCT/IB2017/052252

(51) Int. Cl.
| | |
|---|---|
| *A61K 31/702* | (2006.01) |
| *C12P 1/04* | (2006.01) |
| *A61P 31/04* | (2006.01) |
| *A61K 31/7016* | (2006.01) |
| *C07H 1/00* | (2006.01) |
| *C12P 19/04* | (2006.01) |
| *C12N 9/10* | (2006.01) |
| *A61K 31/716* | (2006.01) |
| *A61K 31/7032* | (2006.01) |

(52) U.S. Cl.
CPC ........ *A61K 31/702* (2013.01); *A61K 31/7016* (2013.01); *A61K 31/7032* (2013.01); *A61K 31/716* (2013.01); *A61P 31/04* (2018.01); *C07H 1/00* (2013.01); *C12N 9/1051* (2013.01); *C12P 1/04* (2013.01); *C12P 19/04* (2013.01); *C07B 2200/13* (2013.01); *Y02A 50/30* (2018.01)

(58) Field of Classification Search
CPC .............. A61K 31/702; A61K 31/7016; A61K 31/7032; A61K 31/706; A61P 31/04; C07H 1/00; C12N 9/1051; C12P 1/04; C12P 19/04

See application file for complete search history.

(56) References Cited

U.S. PATENT DOCUMENTS

| | | | | |
|---|---|---|---|---|
| 8,993,740 | B2* | 3/2015 | Bajza ..................... | A23L 33/10 |
| | | | | 536/17.5 |
| 10,005,807 | B2* | 6/2018 | Chassagne ............... | C07H 5/04 |
| 10,407,516 | B2* | 9/2019 | Chassagne ............ | C08B 37/006 |
| 10,696,705 | B2* | 6/2020 | Matwiejuk ............ | A23L 33/125 |
| 2019/0248824 | A1* | 8/2019 | Chassagne ............... | C07H 1/00 |

FOREIGN PATENT DOCUMENTS

| | | |
|---|---|---|
| EP | 0577580 A2 | 1/1994 |
| EP | 1405856 A1 | 4/2004 |
| EP | 2522232 A1 | 11/2012 |
| WO | 0104341 A1 | 1/2001 |
| WO | 2007101862 A1 | 9/2007 |
| WO | 2010115934 A1 | 10/2010 |
| WO | 2010115935 A1 | 10/2010 |
| WO | 2011100979 A1 | 8/2011 |
| WO | 2011100980 A1 | 8/2011 |
| WO | 2012112777 A2 | 8/2012 |
| WO | 2012155916 A1 | 11/2012 |
| WO | 2012156897 A1 | 11/2012 |
| WO | 2012156898 A1 | 11/2012 |
| WO | 2013044928 A1 | 4/2013 |
| WO | 2013091660 A1 | 6/2013 |
| WO | 2013139344 A1 | 9/2013 |
| WO | 2013185780 A1 | 12/2013 |
| WO | 2014153253 A1 | 9/2014 |
| WO | 2014187464 A1 | 11/2014 |
| WO | 2015036138 A1 | 3/2015 |

(Continued)

OTHER PUBLICATIONS

Murata, T. et al "Facile enzymatic conversion of lactose . . . " Glyconj. J., vol. 16, p. 189-195. (Year: 1999).*
Baumgartner, F. et al., "Galactose-limited fed-batch cultivation of *Escherichia coli* for theproduction of lacto-N-tetraose," Enzyme and Microbial Technology, 2015, vol. 75-76, pp. 37-43.
Baumgartner, F. et al., "Synthesis of the Human Milk Oligosaccharide Lacto-N-Tetraose in Metabolically Engineered, Plasmid-Free *E coli*,"ChemBioChem, 2014, vol. 15, pp. 1896-1900.
Gebus, C. et al., "Synthesis of α-galactosyl epitopes by metabolically engineered *Escherichia coli*," Carbohydrate Research, 2012, vol. 361, pp. 83-90.

(Continued)

*Primary Examiner* — Leigh C Maier
(74) *Attorney, Agent, or Firm* — Neal, Gerber & Eisenberg LLP

(57) ABSTRACT

The present disclosure relates to synthetic mixtures of certain human milk oligosaccharides and uses thereof. Particular mixtures provided herein include: lacto-N-triose II, lacto-N-neotetraose, para-lacto-N-neohexaose, and, optionally, lactose; and lacto-N-triose II, lacto-N-tetraose, para-lacto-N-hexaose II, and, optionally, lactose. These mixtures are useful in the prevention and treatment of viral and bacterial infections.

19 Claims, No Drawings

(56) References Cited

FOREIGN PATENT DOCUMENTS

WO     2015049331 A1    4/2015
WO     2015197082 A1    12/2015
WO     2016008602 A1    1/2016

OTHER PUBLICATIONS

Morales, V. et al., "Rapid Separation on Activated Charcoal of High Oligosaccharides in Honey," Chromatographia, 2006, vol. 64, pp. 233-238.

Priem, B. et al., "A new fermentation process allows large-scale production of human milk oligosaccharides by metabolically engineered bacteria," Glycobiology, 2002, vol. 12(4), pp. 235-240.

Samain, E. et al., "Production of O-acetylated and sulfated chitooligosaccharides by recombinant *Escherichia coli* strains harboring different combinations of nod genes," Journal of Biotechnology, 1999, vol. 72, pp. 33-47.

Whistler, R.L. et al., "Chromatographic Separation of Sugars on Charcoal," J. Am. Chem. Soc., 1950, vol. 72(2), pp. 677-679.

Urashima, T. et al. (2011) Nutrition and Diet Research Progress: Milk Oligosaccharides. New York: Nova Science Publishers, Inc, 92 pages.

Pickard, J.M. et al., "Gut Microbiota: Role in Pathogen Colonization, Immune Responses and Inflammatory Disease," Immunol Rev., 2017, vol. 279(1), pp. 70-89.

\* cited by examiner

COMPOSITIONS COMPRISING HMOS, THEIR PRODUCTION AND USE FOR THE PREVENTION AND/OR TREATMENT OF VIRAL AND/OR BACTERIAL INFECTIONS

CROSS-REFERENCE TO RELATED APPLICATION

This application is a national stage entry pursuant to 35 U.S.C. § 371 of International Application No. PCT/IB2017/053760, filed on Jun. 23, 2017, which claims priority to International Application No. PCT/IB2017/052252, filed on Apr. 19, 2017, which claims priority to EP Patent Application No. 16176257.0, filed on Jun. 24, 2016, and EP Patent Application No. 16176285.1, filed on Jun. 24, 2016, the contents of all of which are fully incorporated herein by reference.

FIELD OF THE INVENTION

The present invention relates to ternary mixtures of human milk oligosaccharides (HMOs), particularly mixtures of a) GlcNAc$\beta$1-3Gal$\beta$1-4Glc (i.e. lacto-N-triose II or LNTri II), b) component A which is Gal$\beta$1-4GlcNAc$\beta$1-3Gal$\beta$1-4Glc (i.e. lacto-N-neotetraose or LNnT) or Gal$\beta$1-3GlcNAc$\beta$1-3Gal$\beta$1-4Glc (i.e. lacto-N-tetraose or LNT), and c) component B which is Gal$\beta$1-4GlcNAc$\beta$1-3Gal$\beta$1-4GlcNAc$\beta$1-3Gal$\beta$1-4Glc (i.e. para-lacto-N-neohexaose or pLNnH) when component A is LNnT or Gal$\beta$1-3GlcNAc$\beta$1-3Gal$\beta$1-3GlcNAc$\beta$1-3Gal$\beta$1-4Glc (i.e. para-lacto-N-hexaose II or pLNH II) and optionally Gal$\beta$1-4Glc (lactose). The invention also relates to a process for making the ternary mixtures, and applications of the ternary mixtures in human health.

BACKGROUND OF THE INVENTION

HMOs have become the subject of much interest in recent years due to their roles in numerous biological processes occurring in the human organism. Mammalian milk contains at least 130 of these complex oligosaccharides (Urashima et al: *Milk Oligosaccharides*, Nova Biomedical Books, New York, 2011, ISBN: 978-1-61122-831-1).

Previously, the only source of HMOs had been mammalian milk which contains mostly water, together with 55-70 g/l lactose, 24-59 g/l lipids, ca. 13 g/l proteins, 5-15 g/l HMOs and ca. 1.5 g/l minerals.

However, efforts to develop processes for synthesizing HMOs have increased significantly in the last ten years due to the roles of HMOs in numerous human biological processes. In this regard, processes have been developed for producing HMOs by microbial fermentations, enzymatic processes, chemical syntheses, or combinations of these technologies. For example, by chemical processes, LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, and 6'-SL and salts thereof can be made as described in WO 2010/100979. As examples of biotechnological processes, WO 01/04341 and WO 2007/101862 describe how to make core human milk oligosaccharides optionally substituted by fucose or sialic acid using genetically modified *E. coli*. As an example of enzymatic processes, sialylated oligosaccharides can be made as described in EP-A-577580.

Efforts have also been made to develop processes for synthesizing enzymatically mixtures of HMOs, without having to synthesize all of the component HMOs of the mixture as described in WO 2012/156897 and WO 2012/156898. Such processes have provided reaction mixtures containing a plurality of different HMOs.

Non-enzymatic processes have also been sought for synthesizing mixtures of HMOs. In this regard, WO 01/04341 described a microbiological process for making a mixture of HMOs. The process involved: i) transforming *E.coli* with foreign genes encoding a $\beta$1,3-N-acetylglucosaminyl transferase and a $\beta$1,4-galactosyl transferase; ii) culturing or fermenting the *E. coli* cell in an aqueous culture medium or fermentation medium containing glycerol and lactose; and then iii) permeabilizing the cell by heat treatment to release its contents of HMOs. The cell contents apparently contained the following two HMOs, LNnT and p-LNnH, as well as para-lacto-N-neooctaose (p-LNnO) and para-lacto-N-neodecaose (p-LNnD), which were separated from each other by Biogel chromatography.

WO 2015/049331 described the application of continuous mode simulated moving bed chromatography with ion exchange resin to separate the neutral HMO LNT produced by bacterial fermentation from other oligosaccharide components.

However, an alternative microbiological process for making a mixture of HMOs which includes LNT or LNnT has been sought in which *E.coli* would secrete the mixture of HMOs out of the cell into the culture medium, without having to permeabilize the cell. Thereby, the HMO mixture could subsequently be readily separated from the culture medium, with minimal contamination of the HMO mixture from, inter alia, cell proteins and cell DNA. Furthermore, an alternative microbiological process has been sought for making a different mixture of HMOs which includes LNT or LNnT and preferably also LNTri II, particularly a mixture which contains a predominant amount of LNT or LNnT, relative to the amounts of other HMOs in the mixture.

SUMMARY OF THE INVENTION

A first aspect of this invention relates to a synthetic mixture of HMOs which comprises, or consists essentially of, a) LNT, pLNH II, LNTri II and optionally lactose, or b) LNnT, pLNnH, LNTri II and optionally lactose. Advantageously, the HMO mixture contains a predominant amount of LNT or LNnT, whichever the case is, relative to the other HMOs and lactose in the mixture. More advantageously, the first HMO mixture has weight ratios of a) lactose, LNTri II and pLNH II relative to LNT:
lactose:LNT is not more than 0.6, LNTri II:LNT is not more than 0.2, and pLNH II:LNT is not more than 0.05; or
b) lactose, LNTri II and pLNnH relative to LNnT:
lactose:LNnT is not more than 0.8, LNTri II:LNnT is not more than 0.1, and pLNnH:LNnT is not ore than 0.4.

A second aspect of this invention relates to a process for making the synthetic HMO mixture of the first aspect of this invention, comprising the steps of:

a) providing a genetically modified cell, advantageously a bacterial cell, more advantageously an *E. coli* cell, comprising:
a first recombinant gene encoding a $\beta$1,3-N-acetylglucosaminyl transferase which is able to transfer a GlcNAc of a UDP-GlcNAc to lactose in the cell and thus to form LNTri II in the cell, and
a second recombinant gene encoding a β1,3- or a β1,4-galactosyl transferase which is able to transfer a galactosyl residue from a UDP-Gal to LNTri II and thus to form LNT or LNnT, respectively, in the cell,
b) culturing the cell in a culture medium containing lactose, thereby inducing:
internalization of the lactose into the cell, preferably via an active transport mechanism, and
formation of LNT, pLNH II and LNTri II, or LNnT, pLNnH and LNTri II, in the cell and then
c) optionally continuing the culturing according to step b) until no lactose is left, and
d) separating and isolating a mixture of LNT, pLNH II, LNTri II and optionally lactose, or that of LNnT, pLNnH, LNTri II and optionally lactose, from the culture medium.

Advantageously, the genetically modified cell has a LacY+, preferably a LacZ−, LacY+, particularly a LacZ−, LacY+, LacI− genotype. Also advantageously, the cell is intact during step c). In one embodiment of step c), a total consumption of lactose is achieved by prolonged fermentation until the cell provided in step a) converts all lactose added in step b) into LNT, pLNH II and LNTri II, or LNnT, pLNnH and LNTri II, whichever the case is. In other embodiment of step c), excess of lactose is hydrolysed enzymatically either by an exogenously added galactosidase or by a galactosidase expressed by the cell provided in step a).

A third aspect of this invention relates to a method for crystallizing
a) LNT wherein the crystallization is carried out from a mixture comprising LNT, LNTri II, pLNH II and optionally lactose which has weight ratios of lactose, LNTri II and pLNH II relative to LNT:
lactose:LNT=0 to 0.2, LNTri II:LNT is not more than 0.15 and pLNH II:LNT is not more than 0.05,
using one or more monohydroxy $C_1$-$C_4$ alcohol(s) as antisolvent(s); or
b) LNnT wherein the crystallization is carried out from a mixture comprising LNnT, LNTri II, pLNnH and optionally lactose which has weight ratios of lactose, LNTri II and pLNnH relative to LNnT:
lactose:LNnT=0 to 0.2, LNTri II:LNnT is not more than 0.1 and pLNnH:LNnT is not more than 0.03,
using one or more monohydroxy $C_1$-$C_4$ alcohol(s) and/or acetone as antisolvent(s)

A fourth aspect of this invention relates to an anti-infective composition for preventing and/or treating viral and/or bacterial infections in a human, comprising LNT, pLNH II and LNTri II, or LNnT, pLNnH and LNTri II, advantageously the synthetic HMO mixtures of the first aspect of this invention. This composition contains a plurality of different HMOs with novel combinations of properties and biological activities. The composition is especially useful against viral and bacterial, intestinal infections through specific modulation of the gastrointestinal microbiota, modulation of intestinal binding of bacteria and viruses and improvement of intestinal barrier function and immune function. In this regard, the composition increases Bifidobacterium abundance of the gastrointestinal microbiota in a human. The composition is also especially useful against viral and bacterial, respiratory tract infections by inhibiting pathogen colonization to protect the host from infection and/or regulating the immune system.

A fifth aspect of this invention relates to a method of modulating the gastrointestinal microbiota of a human to increase Bifidobacterium abundance. The method comprises administering, to the human, LNT, pLNH II and LNTri II, or LNnT, pLNnH and LNTri II, advantageously the synthetic HMO mixture of the first aspect of this invention.

A sixth aspect of this invention relates to a method of preventing or treating viral and/or bacterial infections in a human, especially intestinal infections and infections of the respiratory tract. The method comprises administering, to the human LNT, pLNH II and LNTri II, or LNnT, pLNnH and LNTri II, advantageously the synthetic HMO mixture of the first aspect of this invention.

DETAILED DESCRIPTION OF THE INVENTION

In accordance with this invention, it has been surprisingly discovered that a synthetic mixture of LNT, pLNH II and LNTri II, or LNnT, pLNnH and LNTri II, and optionally lactose, can provide an anti-infective composition for treating and/or preventing viral and/or bacterial infections of the intestinal and respiratory tracts of humans. The mixture acts through specific modulation of the microbiota in the intestinal tract. In this regard, the mixture increases Bifidobacterium abundance and may also reduce Firmicutes, especially Clostridia, abundance of the microbiota. The mixture also inhibit colonization of a range of respiratory pathogens by stimulating the host defences including modulation of the immune system.

In addition, it has been surprisingly discovered, that a mixture of LNT, pLNH II and LNTri II, or LNnT, pLNnH and LNTri II, and optionally lactose, can be advantageously used for selective crystallization of LNT or LNnT from the corresponding mixture. The isolation process of LNT or LNnT from the culturing broth can be facilitated and simplified by eliminating costly and cumbersome separation techniques, such as Biogel chromatography and simulated moving bed chromatography proposed by the prior art that are suitable for separating carbohydrate components from each other. Instead, it is sufficient to separate a mixture of LNT, pLNH II and LNTri II, or LNnT, pLNnH and LNTri II, and optionally lactose, from which LNT or LNnT, respectively, is readily obtainable by selective crystallization.

The term "synthetic mixture" or "synthetic composition" designates a mixture or composition which is artificially prepared and preferably mean a mixture or composition containing at least one compound that is produced ex vivo chemically and/or biologically, e.g. by means of chemical reaction, enzymatic reaction or recombinantly. In this regard, "synthetic" is used as opposite to "natural", and means that a synthetic mixture or composition of the invention is not identical to a natural composition or mixture, like human milk, or at least one HMO of the mixture or the composition is not originated from a natural source, like e.g. human milk.

First Aspect of the Invention

The mixture of this invention is an HMO mixture comprising, preferably consisting essentially of:
GlcNAcβ1-3Galβ1-4Glc (LNTri II),
a component A which is Galβ1-3GlcNAcβ1-3Galβ1-4Glc (LNT) or Galβ1-4GlcNAcβ1-3Galβ1-4Glc (LNnT),
a component B which is:
Galβ1-3GlcNAcβ1-3 Galβ1-3GlcNAcβ1-3Galβ1-4Glc (pLNH II) when component A is LNT, or Galβ1-4GlcNAcβ1-3 Galβ1-4GlcNAcβ1-3Galβ1-4Glc (pLNnH) when component A is LNnT, and optionally lactose.

The term "optionally" in the present context means that lactose is either present in the mixture or not. In this regard, the mixture of the invention, in one embodiment, may be a mixture comprising, preferably consisting essentially of LNT, pLNH II, LNTri II and lactose, in other embodiment a mixture comprising, preferably consisting essentially of LNnT, pLNnH, LNTri II and lactose. Moreover, the mixture of the invention may be a mixture comprising, preferably consisting essentially of LNT, pLNH II and LNTri II, or a mixture comprising, preferably consisting essentially of LNnT, pLNnH and LNTri II. Each mixture of this invention preferably contains a predominant amount of LNT or LNnT, whichever the case is, relative to the amount of each of the pLNH II and LNTri II, or pLNnH and LNTri II, respectively, and any lactose in the mixtures, more preferably relative to the total amount of the pLNH II, LNTri II and any lactose, or pLNnH, LNTri II and any lactose, respectively, in the mixtures. In case of a mixture comprising LNnT, it is also preferred that the mixture contains substantially no p-LNnO or p-LNnD. By the term "predominant" is meant that the amount of LNT or LNnT, whichever the case is, by weight in a mixture of this invention is greater than the amount of each of the pLNH II and LNTri II, or pLNnH and LNTri II, respectively, and any lactose, such the amount of LNT is at least about 2.5 times greater, or at least about 5 times greater, or at least about 10 times greater than the amount of each of the pLNH II and LNTri II and any lactose, or the combined amount of each of the pLNH II and LNTri II and any lactose, in the mixture, or the amount of LNnT is at least about 2.5 times greater, or at least about 5 times greater, or at least about 10 times greater than the amount of each of the pLNnH and LNTri II and any lactose, or the combined amount of each of the pLNnH and LNTri II and any lactose, in the mixture.

In the HMO mixture, the weight ratios of lactose, LNTri II and pLNH II relative to LNT are preferably:

lactose:LNT is 0 to not more than 0.6, LNTri II:LNT is not more than 0.2 and pLNH II:LNT is not more than 0.05.

In the HMO mixture, the weight ratios of lactose, LNTri II and pLNnH relative to LNnT are preferably:

lactose:LNnT is 0 to not more than 0.8, LNTri II:LNnT is not more than 0.1 and pLNnH:LNnT is not more than 0.4.

According to the above definition of the HMO mixture of the first aspect, lactose is an optional ingredient, which means that the ratio of lactose:LNT is 0 to 0.6, and the ratio of lactose:LNnT is 0 to 0.8. When this ratio is 0, the HMO mixture of the invention does not contain lactose, or at least substantially does not contain lactose (that is substantially lactose-free). When the HMO mixture of the invention contains lactose, its weight ratio to LNT is higher than 0 but not more than 0.6, or its weight ratio to LNnT is higher than 0 but not more than 0.8. On the other hand, the both LNTri II:LNT and the pLNH II:LNT ratios, in the LNT containing mixture, are higher than 0, or both LNTri II:LNnT and the pLNnH:LNnT ratios, in the LNnT containing mixture, are higher than 0 (in other words: cannot be 0), because both LNTri II and pLNH II, or both LNTri II and pLNnH, whichever the case is, are essential components of the claimed HMO mixtures.

In certain embodiments of the first aspect, the weight ratios of lactose, LNTri II and pLNH II relative to LNT are:

lactose:LNT is not more than 0.4, LNTri II:LNT is not more than 0.2 and pLNH II:LNT is not more than 0.05, or lactose:LNT is 0, LNTri II:LNT is not more than 0.2 and pLNH II:LNT is not more than 0.05, or lactose:LNT is not more than 0.4, LNTri II:LNT is not more than 0.15 and pLNH II:LNT is not more than 0.03, or lactose:LNT is 0, LNTri II:LNT is not more than 0.15 and pLNH II:LNT is not more than 0.03, or lactose:LNT=0.15 to 0.20, LNTri II:LNT=0.05 to 0.12 and pLNH II:LNT=0.005 to 0.03, or lactose:LNT is 0, LNTri II:LNT=0.05 to 0.12 and pLNH II:LNT=0.005 to 0.03, or lactose:LNT=0.10 to 0.15, LNTri II:LNT=0.04 to 0.1 and pLNH II:LNT=0.005 to 0.03, or lactose:LNT is 0, LNTri II:LNT=0.04 to 0.1 and pLNH II:LNT=0.005 to 0.03.

In further certain embodiments of the first aspect, the weight ratios of lactose, LNTri II and pLNnH relative to LNnT are:

lactose:LNnT is not more than 0.4, LNTri II:LNnT is not more than 0.1 and pLNnH:LNnT is not more than 0.4, or lactose:LNnT is 0, LNTri II:LNnT is not more than 0.1 and pLNnH:LNnT is not more than 0.4, or lactose:LNnT is not more than 0.4, LNTri II:LNnT is not more than 0.05 and pLNnH:LNnT is not more than 0.2, or lactose:LNnT is 0, LNTri II:LNnT is not more than 0.05 and pLNnH:LNnT is not more than 0.2, or lactose:LNnT=0.37 to 0.72, LNTri II:LNnT=0.01 to 0.05 and pLNnH:LNnT=0.15 to 0.25, or lactose:LNnT is 0, LNTri II:LNnT=0.01 to 0.05 and pLNnH:LNnT=0.15 to 0.25, or lactose:LNnT=0.43 to 0.72, LNTri II:LNnT=0.02 to 0.04 and pLNnH:LNnT=0.15 to 0.20, or lactose:LNnT is 0, LNTri II:LNnT=0.02 to 0.04 and pLNnH:LNnT=0.15 to 0.20, or lactose:LNnT=0.43 to 0.72, LNTri II:LNnT=0.03 to 0.05 and pLNnH:LNnT=0.18 to 0.19, or lactose:LNnT is 0, LNTri II:LNnT=0.03 to 0.05 and pLNnH:LNnT=0.18 to 0.19.

In other embodiments, the synthetic HMO mixture, which is advantageously suitable for selective crystallization of LNT, has the weight ratios of lactose, LNTri II and pLNH II relative to LNT:

lactose:LNT=0 to 0.2, LNTri II:LNT is not more than 0.15 and pLNH II:LNT is not more than 0.05, such as lactose:LNT is 0 to 0.2, LNTri II:LNT is not more than 0.12 and pLNH II:LNT is not more than 0.03, or lactose:LNT=0 to 0.2, LNTri II:LNT is not more than 0.1 and pLNH II:LNT is not more than 0.02, or lactose:LNT=0 to 0.2, LNTri II:LNT is not more than 0.075 and pLNH II:LNT is not more than 0.01.

In other embodiments, the synthetic HMO mixture, which is advantageously suitable for selective crystallization of LNnT, has the weight ratios of lactose, LNTri II and pLNnH relative to LNnT:

lactose:LNnT=0 to 0.2, LNTri II:LNnT is not more than 0.1 and pLNnH:LNnT is not more than 0.03, such as lactose:LNnT is 0 to 0.2, LNTri II:LNnT=0.005 to 0.1 and pLNnH:LNnT=0.005 to 0.03, or lactose:LNnT=0 to 0.2, LNTri II:LNnT=0.005 to 0.05 and pLNnH:LNnT=0.005 to 0.025, or lactose:LNnT=0 to 0.2, LNTri II:LNnT=0.01 to 0.03 and pLNnH:LNnT=0.01 to 0.025.

Second Aspect of the Invention

The HMO mixtures of this invention can be readily obtained by a process which involves culturing or fermenting a genetically modified cell in an aqueous culture medium or fermentation medium containing lactose and one or more carbon-based substrates followed by separating them from the culture medium. By the term "culture medium" is meant the aqueous environment of the fermentation process in a fermenter outside of the genetically modified cell.

By the term "genetically modified cell" is preferably meant a cell in which at least one DNA sequence has been added to, deleted from or changed in the cell's genome, so that the cell has a changed phenotype. This change in phenotype alters the characteristics of the genetically modified cell from that of the wild type cell. Thus, the genetically modified cell can perform at least an additional chemical transformation, when cultured or fermented, due to the added or changed DNA that encodes the expression of at least one enzyme not found in the wild type cell, or the genetically modified cell cannot perform a chemical transformation due to the deleted, added or changed DNA that encodes the expression of an enzyme found in the wild type cell. The genetically modified cell can be produced by conventional genetic engineering techniques. The genetically modified cell can be a bacteria or yeast but preferably is a bacteria. Preferred bacteria include *Escherichia coli, Bacillus* spp. (e.g. *B. subtilis*), *Campylobacter pylori, Helicobacter pylori, Agrobacterium tumefaciens, Staphylococcus aureus, Thermophilus aquaticus, Azorhizobium caulinodans, Rhizobium leguminosarum, Neisseria gonorrhoeae, N. meningitis, Lactobacillus* spp., *Lactococcus* spp., *Enterococcus* spp., *Bifidobacterium* spp., *Sporolactobacillus* spp., *Micromomospora* spp., *Micrococcus* spp., *Rhodococcus* spp., *Pseudomonas*, particularly *E. coli*.

Specifically, the genetically modified cell of this invention contains:
  a first recombinant gene encoding a β1,3-N-acetyl-glucosaminyl transferase which is able to transfer a GlcNAc of a UDP-GlcNAc to lactose and thereby to form LNTri II in the cell,
  a second recombinant gene encoding
    either a β1,3-galactosyl transferase which is able to transfer a galactosyl residue from a UDP-Gal to LNTri II thereby to form LNT in the cell,
    or a β1,4-galactosyl transferase which is able to transfer a galactosyl residue from a UDP-Gal to LNTri II thereby to form LNnT in the cell.

A preferred genetically modified cell has a LacZ$^-$, particularly a LacZ$^-$, LacY$^+$, more particularly a LacZ$^-$, LacY$^+$, LacI$^-$ genotype.

The genetically modified cell in this invention, when cultured in the aqueous culture medium containing lactose, can internalize the lactose and then transfer a GlcNAc residue of an activated sugar nucleotide in the cell to the internalized lactose to form LNTri II in the cell. The cell can also transfer a galactosyl residue of an activated sugar nucleotide in the cell to the previously formed LNTri II in the cell to form LNT or LNnT, whichever the case is, in the cell. The recombinant genes or the equivalent DNA sequences responsible for these transfers can be introduced into the cell in a well known manner, using conventional expression vectors. The origin of these heterologous nucleic acid sequences can be, for example, any bacteria, such as *N. meningitidis* or *H. pylori*.

In carrying out this process, the genetically modified cell is cultured in the presence of a carbon-based substrate such as glycerol, glucose, sucrose, glycogen, fructose, maltose, starch, cellulose, pectin, chitin, etc. Preferably, the cell is cultured with glycerol, glucose, sucrose and/or fructose.

This process also involves initially transporting the exogenous lactose from the culture medium into the genetically modified cell. Lactose can be added exogenously in a conventional manner to the culture medium, from which it can then be transported into the cell. The internalization of lactose should not, of course, affect the basic and vital functions or destroy the integrity of the cell. The internalization can take place via a passive transport mechanism during which lactose diffuses passively across the plasma membrane of the cell. The flow is directed by the concentration difference in the extra- and intracellular space with respect to lactose to be internalized, so that lactose passes from the place of higher concentration to the place of lower concentration. However, lactose is preferably internalized in the cell with the aid of an active transport mechanism, by which lactose diffuses across the plasma membrane of the cell under the influence of a transporter protein or lactose permease (LacY) of the cell.

In some embodiments, the genetically modified cell used in this process lacks enzymatic activity which would significantly degrade lactose, LNT, LNnT, LNTri II, pLNH II, pLNnH and the metabolic intermediates needed to make LNT, LNnT, LNTri II and pLNH II and pLNnH in the cell. In this regard, the native β-galactosidase of the culturing cell (encoded by the LacZ gene in *E. coli*), which hydrolyses lactose to galactose and glucose, is preferably deleted or inactivated (LacZ$^-$ genotype). In one embodiment of the second aspect of the invention, excess of lactose added in step b) is not removed or degraded after fermentation and a mixture of lactose, LNT, LNTri II and pLNH II, or a mixture of lactose, LNnT, LNTri II and pLNnH, whichever the case is, is separated and isolated from the culture medium according to step d), giving rise to an HMO mixture consisting essentially of lactose, LNT, LNTri II and pLNH II, or an HMO mixture consisting essentially of lactose, LNnT, LNTri II and pLNnH, respectively. In other embodiment, a mixture of lactose, LNT, LNTri II and pLNH II, or mixture of lactose, LNnT, LNTri II and pLNnH, is produced by fermentation as above, and a mixture of LNT, LNTri II and pLNH II, or a mixture of LNnT, LNTri II and pLNnH, whichever the case is, is separated and isolated from the culture milieu and from the excess of lactose, giving rise to an HMO mixture consisting essentially of LNT, LNTri II and pLNH II, or an HMO mixture consisting essentially of LNnT, LNTri II and pLNnH, respectively. Yet in other embodiment, a mixture of lactose, LNT, LNTri II and pLNH II, or a mixture of lactose, LNnT, LNTri II and pLNnH, is produced by fermentation as above, and followed by, in step c),
  i) addition of a lactose degrading enzyme, e.g. a galactosidase, exogenously which hydrolyses lactose into monosaccharides, or
  ii) letting the fermentation continue until all lactose added in step b) are converted into the desired HMOs,
  providing a substantially lactose-free broth. In this regard, in option ii), a genetically modified cell of LacZ$^-$ genotype disclosed above can further comprise a functional recombinant β-galactosidase. This functional galactosidase may be encoded by an exogenous LacZ gene which is heat inducible (see e.g. WO 2015/036138). At the temperature of the fermentation this functional β-galactosidase is not expressed by the cell, therefore the internalized lactose is not degraded in the cell during while the HMOs are produced. When the desired concentration or amount of HMOs in the broth are reached, the culturing is continued at elevated temperature by which the functional β-galactosidase is expressed and the lactose in excess is degraded. Alternatively, a genetically modified cell of LacZ$^-$ genotype disclosed above may comprise a recombinant β-galactosidase of low but detectable level of activity (see e.g. WO 2012/112777) in order to remove the optional residual lactose at the end of fermentation. Both alternatives thus provide a substantially lactose-free broth containing LNT, LNTri II and pLNH II, or a substantially lactose-free broth containing LNnT, LNTri II and pLNnH, from which an HMO mixture consisting essentially of LNT, LNTri II and pLNH II, or an HMO mixture consisting essentially of LNnT, LNTri II and pLNnH, respectively, can be readily separated and isolated.

Further examples of LNT producing strains are disclosed in e.g. Baumgärtner et al. *ChemBioChem* 15, 1896 (2014) and *Enzyme Microb. Technol.* 75-76, 37 (2015), WO 2014/153253, WO 2015/036138 or WO 2016/008602. Further examples of LNnT producing strains are disclosed in e.g. Priem et al. *Glycobiology* 12, 235 (2002), Gebus et al. *Carbohydr. Res.* 361, 83 (2012), WO 01/04341, WO 2014/153253, WO 2015/197082 or WO 2016/008602.

For high yields, the process preferably involves providing, in the culture medium, a carbon-based substrate and at least 30, preferably at least 45, more preferably 50 to 70, up to about 100, grams of lactose per liter of the initial volume of the culture medium. Preferably, the process is also carried out at a temperature of 28 to 35° C., preferably with continuous agitation and continuous aeration for more than 2½ days, more preferably at least 4 days. It is further preferred that the final volume of the culture medium is not more than three-fold, more preferably not more than two-fold, more preferably less than two-fold, of the volume of the initial volume of the culture medium before providing lactose and the carbon-based substrate to the culture medium.

According to an embodiment in carrying out the process of the invention, a genetically modified $LacZ^-Y^+$ *E. coli* strain is cultured in the following way:

(1) a first phase of exponential cell growth that is ensured by a carbon-based substrate, preferably glucose, provided in the culture medium and that preferably lasts until the glucose has all been consumed which is preferably at least 12 hours, more preferably at least 18 hours, still more preferably 20-25 hours, up to about 48 hours; and (2) a second phase of cell growth that is limited by a carbon-based substrate, preferably glycerol, and lactose which are provided, preferably continuously, in the culture medium after the first phase and that lasts until the glucose and preferably most (e.g. at least 60%) of the lactose have been consumed which is preferably at least 35 hours, more preferably at least 45 hours, still more preferably 50 to 70 hours, up to about 130 hours.

The LNnT, LNTri II, pLNnH and optionally lactose mixture that is produced extracellularly in the aqueous culture medium by the above process comprises at least 20, more preferably at least 30, even more preferably at least 40 grams, yet more preferably particularly at least 50 grams of LNnT, per liter of the final volume of the culture medium. In the mixture of LNnT, LNTri II, pLNnH and lactose in the culture medium, the lactose is predominantly unreacted lactose that has not been transported from the culture medium into the genetically modified cell.

During culturing of the genetically modified cell, LNT, LNnT, LNTri II, pLNH II and pLNnH accumulate in both the cell's intracellular and extracellular matrices, preferably predominantly in the extracellular matrix. A predominant portion of this mixture is then transported outside the cell to the aqueous culture medium in a passive way, i.e. it diffuses outside the cell across the cell membrane. This transport can be enhanced by providing, in the cell, one or more sugar efflux transporters, i.e. proteins that promote the effluence of sugar derivatives from the cell to the culture medium (see e.g. WO 2010/142305). The sugar efflux transporter(s) can be overexpressed under the conditions of the fermentation to enhance the export, to the culture medium, of this mixture produced in the cell.

The LNT, LNTri II and pLNH II product mixture, which are transported from the cell to the aqueous culture medium, preferably contains a predominant amount of LNT. More preferably in the culture medium, the LNT, LNTri II, pLNH II and optionally lactose are present in the following ratios:

lactose:LNT is not more than 0.6, LNTri II:LNT is not more than 0.2 and pLNH II:LNT is not more than 0.05, such as lactose:LNT is not more than 0.4, LNTri II:LNT is not more than 0.2 and pLNH II:LNT is not more than 0.05, or lactose:LNT is not more than 0.2, LNTri II:LNT is not more than 0.2 and pLNH II:LNT is not more than 0.05, or lactose:LNT is not more than 0.4, LNTri II:LNT is not more than 0.15 and pLNH II:LNT is not more than 0.03, or lactose:LNT is not more than 0.2, LNTri II:LNT is not more than 0.15 and pLNH II:LNT is not more than 0.03, or lactose:LNT=0.15 to 0.20, LNTri II:LNT=0.05 to 0.12 and pLNH II:LNT=0.005 to 0.03, or lactose:LNT=0.10 to 0.15, LNTri II:LNT=0.04 to 0.1 and pLNH II:LNT=0.005 to 0.03.

LNT, LNTri II, pLNH II and optionally lactose can then be separated in a conventional manner from the cells and impurities in the culture medium and, optionally, the mixture of LNT, LNTri II and pLNH II from the lactose in the culture medium.

The LNnT, LNTri II and pLNnH product mixture, which are transported from the cell to the aqueous culture medium, preferably contains a predominant amount of LNnT. More preferably in the culture medium, the LNnT, LNTri II, pLNnH and optionally lactose are present in the following ratios:

lactose:LNnT is not more than 0.8, LNTri II:LNnT is not more than 0.05 and pLNnH:LNnT is not more than 0.4, such as lactose:LNnT=0.2 to 0.8, LNTri II:LNnT is not more than 0.05 and pLNnH:LNnT is not more than 0.4, or lactose:LNnT=0.37 to 0.72, LNTri II:LNnT=0.03 to 0.05 and pLNnH:LNnT=0.15 to 0.25, or lactose:LNnT=0.43 to 0.72, LNTri II:LNnT=0.03 to 0.05 and pLNnH:LNnT=0.15 to 0.20, or lactose:LNnT=0.43 to 0.72, LNTri II:LNnT=0.03 to 0.05 and pLNnH:LNnT=0.18 to 0.19, or lactose:LNnT is not more than 0.2, LNTri II:LNnT=0.03 to 0.05 and pLNnH:LNnT=0.15 to 0.25, or lactose:LNnT is not more than 0.2, LNTri II:LNnT=0.03 to 0.05 and pLNnH:LNnT=0.15 to 0.20, or lactose:LNnT is not more than 0.2, LNTri II:LNnT=0.03 to 0.05 and pLNnH:LNnT=0.18 to 0.19.

LNnT, LNTri II, pLNnH and optionally lactose can then be separated in a conventional manner from the cells and impurities in the culture medium and, optionally, the mixture of LNnT, LNTri II and pLNnH from the lactose in the culture medium.

Step d) of the second aspect of the invention comprises at least one of the the following separation steps:
  ultrafiltration,
  nanofiltration,
  ion exchange treatment, or
  active charcoal treatment,
but preferably two or three of them, or all four steps, in any order. Advantageously, an ultrafiltration step is always comprised, preferably as the first separation step (that is applied on the fermentation broth), followed by nanofiltration, ion exchange treatment and/or active charcoal treatment.

A first separation step involves separating the aqueous culture medium, containing LNT, LNTri II, pLNH II and optional lactose, or LNnT, LNTri II, pLNnH and optional lactose, from the cells and from suspended particulates and contaminants, insoluble materials and debris. In this step, the culture medium can be clarified in a conventional manner, for example by membrane filtration or centrifugation of the broth. According to an embodiment, the membrane filtration is ultrafiltration (UF). In the ultrafiltration step separates the biomass and, preferably also high molecular weight suspended solids, from the soluble components of the broth. An aqueous solution containing the produced LNT, LNTri II, pLNH II and optionally lactose, or LNnT, LNTri II, pLNnH and optionally lactose, without substantially changing their relative weight ratios to each other, passes through the ultrafiltration membrane giving rise to the UF permeate (UFP).

Any conventional ultrafiltration membrane can be used having a molecular weight cut-off (MWCO) range between about 1 and about 500 kDa, such as 10-250, 50-100, 200-500, 100-250, 1-100, 1-50, 10-25, 1-5 kDa, any other suitable sub-ranges. The membrane material can be a ceramic or made of a synthetic or natural polymer, e.g. polysulfone, polypropylene, cellulose acetate or polylactic acid. The ultrafiltration step can be applied in dead-end or cross-flow mode. This separation step may comprise more than one ultrafiltration step using membranes with different MWCO, e.g. using two ultrafiltration separations wherein the first membrane has a higher MWCO than that of the second membrane. This arrangement may provide a better separation efficacy of the higher molecular weight components of the broth. After this separation step the permeate contains materials that have a molecular weight lower than the MWCO of the second membrane, including the moxture of LNT, LNTri II, pLNH II and optionally lactose or LNnT, LNTri II, pLNnH and optionally lactose, in substantially the same range as before applying the UF step.

A second separation step comprises nanofiltration (NF). This nanofiltration step may advantageously be used to concentrate the previously obtained UFP and/or to remove ions, mainly monovalent ions, and organic materials having a molecular weight lower than that of lactose, such as monosaccharides. The nanofiltration membrane has a MWCO that ensures the retention of LNT, LNnT, LNTri II, pLNH II and pLNnH, that is its MWCO is lower than that of the ultrafiltration membrane(s) used in the previous step, and around 25-50% of the molecular weight of LNTri II, LNT or LNnT. In this regard LNT, LNTri II and pLNH II, or LNnT, LNTri II and pLNnH, are accumulated in the NF retentate (NFR). Interestingly, most of the lactose (if present) is also retained in the NFR, thus amounts of LNT, LNTri II, pLNH II and optionally lactose, or LNnT, LNTri II, pLNnH and optionally lactose, are in substantially the same range as before applying the NF step. The nanofiltration can be combined with diafiltration with water in order to remove permeable molecules more effectively, e.g. until the conductivity of the permeate showing no or very low presence of salts.

A third separation step preferably involves removing any remaining minerals, salts and other charged molecules, as well as amino acids, from the remaining culture medium, preferably after the second separation step. This third separation step can be carried out in a conventional manner, using ion exchange resin(s), by passing the remaining culture medium through a cation exchange resin in H$^+$-form and/or an anion exchange resin in free base form. The cation exchange resin is preferably a strong exchanger, and the anion exchange resin is a weak exchanger. The ion exchange resins, besides removing salts and charged molecules from the remaining culture medium, can physically adsorb proteins, DNA and colorizing/caramel bodies that were left in the second HMO mixture in the remaining culture medium.

According to one embodiment, the ion exchange resin is an anion exchange resin, preferably a weakly basic anion exchange resin. In this step the negatively charged materials can be removed from the pre-treated solution as they bind to the resin. The aqueous solution of LNT, LNTri II, pLNH II and optionally lactose, or LNnT, LNTri II, pLNnH and optionally lactose, is contacted with an anion exchange resin in any suitable manner which would allow the negatively charged materials to be adsorbed onto the anion exchange resin, and the neutral oligosaccharides to pass through. The resulting liquid, after contacting with the anion exchange resin, contains primarily water, cations and the mixture of LNT, LNTri II, pLNH II and optionally lactose, or LNnT, LNTri II, pLNnH and optionally lactose.

According to another embodiment, the ion exchange resin is a cation exchange resin, preferably a strongly acidic cation exchange resin. In this step the positively charged materials can be removed from the pre-treated solution as they bind to the resin. The solution of LNT, LNTri II, pLNH II and optionally lactose, or LNnT, LNTri II, pLNnH and optionally lactose, is contacted with the cation exchange resin in any suitable manner which would allow positively charged materials to be adsorbed onto the cation exchange resin, and the neutral oligosaccharides to pass through. The resulting liquid, after contacting with the cation exchange resin, contains primarily water, LNT, LNTri II, pLNH II and optionally lactose, or LNnT, LNTri II, pLNnH and optionally lactose besides anions.

One of the ion exchange resin treatments disclosed above may be sufficient to obtain the mixture of LNT, LNTri II, pLNH II and optionally lactose, or LNnT, LNTri II, pLNnH and optionally lactose, in a required purity. If necessary, both cation and anion exchange resin chromatography, in any order, can be applied. The ion exchange resin treatment does not change substantially the relative weight ratios of LNT, LNTri II, pLNH II and optionally lactose, or LNnT, LNTri II, pLNnH and optionally lactose, in the mixture.

When using an ion exchange resin, its degree of cross-linking can be chosen depending on the operating conditions of the ion exchange column. A highly crosslinked resin offers the advantage of durability and a high degree of mechanical integrity, however suffers from a decreased porosity and a drop off in mass-transfer. A low-crosslinked resin is more fragile and tends to swell by absorption of mobile phase. The particle size of the ion exchange resin is selected to allow an efficient flow of the eluent, while the charged materials are still effectively removed. A suitable flow rate may also be obtained by applying a negative pressure to the eluting end of the column or a positive pressure to the loading end of the column, and collecting the eluent. A combination of both positive and negative pressure may also be used. The ion exchange treatment can be carried out in a conventional manner, e.g. batch-wise or continuously.

Non-limiting examples of a suitable acidic cation exchange resin can be e.g. Amberlite IR100, Amberlite IR120, Amberlite FPC22, Dowex 50WX, Finex CS16GC, Finex CS13GC, Finex CS12GC, Finex CS11GC, Lewatit S, Diaion SK, Diaion UBK, Amberjet 1000, Amberjet 1200.

Non-limiting examples of a suitable basic anion exchange resin can be e.g. Amberlite IRA67, Amberlite IRA 96, Amberlite IRA743, Amberlite FPA53, Diaion CRB03, Diaion WA10, Dowex 66, Dowex Marathon, Lewatit MP64.

A fourth separation step preferably involves removing any remaining colorizing/caramel bodies and/or water soluble contaminants, such as salts, from the remaining culture medium. This fourth step can be carried out in a conventional manner, using activated charcoal, to decolour the HMO mixture obtained in a previous step. The active charcoal treatment may follow any of the ultrafiltration, nanofiltration or ion exchange treatment disclosed above, preferably the ion exchange treatment.

A carbohydrate substances like LNT, LNnT, LNTri II, pLNH II, pLNnH and lactose (if present) tend to be bound to the surface of charcoal particles from their aqueous solution, e.g. an aqueous solution obtained after UF, NF or ion exchange treatment. Similarly, the colorizing agents are also capable or adsorbing to the charcoal. While the carbohydrates and colour giving materials are adsorbed, water soluble materials that are not or weaker bound to the charcoal can be eluted with water. By changing the eluent from water to aqueous ethanol, the adsorbed carbohydrates can easily be eluted and collected, the mixture having substantially the same relative weight ratios with regard to LNT, LNTri II, pLNH II and optionally lactose, or LNnT, LNTri II, pLNnH and optionally lactose. The adsorbed colour giving substances would remain adsorbed on the charcoal, thus both decolourization and desalination can be achieved simultaneously in this step.

Under certain conditions, the LNT, LNTri II, pLNH II and lactose (if present), or LNnT, LNTri II, pLNnH and lactose (if present) are not, or at least not substantially, adsorbed to the charcoal particles and elution with water gives rise to an aqueous solution of those oligosaccharides without a significant loss in their amounts, while the colour giving substances remain adsorbed. It is a matter of routine skills to determine the conditions under which the oligosaccharides would bind to the charcoal from its aqueous solution. For example, in one embodiment a more diluted solution of LNT, LNTri II, pLNH II and lactose (if present), or LNnT, LNTri II, pLNnH and lactose (if present), is used, in another embodiment a lower amount of charcoal relative to the amount of the oligosaccharides is applied. In this embodiment the weight ratios of LNT, LNTri II, pLNH II and optionally lactose, or LNnT, LNTri II, pLNnH and optionally lactose, are in substantially the same range as before applying this particular active charcoal treatment.

Yet in one embodiment of active charcoal treatment, when the lactose:LNT ratio higher that 0.2 in the mixture of LNT, LNTri II, pLNH II and lactose obtained in the fermentation process and/or after any of the separation steps disclosed above can be reduced to 0.2 or below by advantageously applying an active charcoal treatment, e.g. by adaption of the method suggested by Whistler et al *J. Am. Chem. Soc.* 72, 677 (1950) or that by Morales et al. *Chromatographia* 64, 233 (2006). The methods are based on the elution/removal of substantial amount of the disaccharide lactose from the higher oligosaccharides LNTri II, LNT and pLNH II, thus the mixture of LNTri II, LNT and pLNH II with low or no lactose content (that is wherein the weight ratio of lactose: LNT is below 0.2) is obtainable, while the weight ratios of LNT to LNTri II and pLNH II do not change substantially. Accordingly, by applying the above active charcoal treatment on an HMO mixture comprising or consisting of LNT, LNTri II, pLNH II and lactose wherein the weight ratios of lactose, LNTri II and pLNH II relative to LNT in the mixture are:

lactose:LNT is more than 0.2 but less than 0.8, LNTri II:LNT is not more than 0.15 and pLNH II:LNT is not more than 0.05, an HMO mixture comprising or consisting of LNT, LNTri II, pLNH II and lactose wherein the weight ratios of lactose, LNTri II and pLNH II relative to LNT in the mixture are:

lactose:LNT=0 to 0.2, LNTri II:LNT is not more than 0.15 and pLNH II:LNT is not more than 0.05, is obtainable, which mixture can be advantageously used for selectively crystallizing out LNT. A mixture in which at least one of the ratios is higher than that defined above is unsuitable mixture for selective crystallization of LNT.

Yet in one embodiment of active charcoal treatment, when the lactose:LNnT ratio higher that 0.2 in the mixture of LNnT, LNTri II, pLNnH and lactose obtained in the fermentation process and/or after any of the separation steps disclosed above can be reduced to 0.2 or below by advantageously applying an active charcoal treatment, e.g. by adaption of the method suggested by Whistler et al *J. Am. Chem. Soc.* 72, 677 (1950) or that by Morales et al. *Chromatographia* 64, 233 (2006). The methods are based on the elution/removal of substantial amount of the disaccharide lactose from the higher oligosaccharides LNTri II, LNnT and pLNnH, thus the mixture of LNTri II, LNnT and pLNnH with low or no lactose content (that is wherein the weight ratio of lactose:LNnT is below 0.2) is obtainable, while the weight ratios of LNnT to LNTri II and pLNnH do not change substantially. Accordingly, by applying the above active charcoal treatment on an HMO mixture comprising or consisting of LNnT, LNTri II, pLNnH and lactose wherein the weight ratios of lactose, LNTri II and pLNnH relative to LNnT in the mixture are:

lactose:LNnT is more than 0.2 but less than 0.8, LNTri II:LNnT is not more than 0.1 and pLNnH:LNnT is not more than 0.03, an HMO mixture comprising or consisting of LNnT, LNTri II, pLNnH and lactose wherein the weight ratios of lactose, LNTri II and pLNnH relative to LNnT in the mixture are:

lactose:LNnT=0 to 0.2, LNTri II:LNnT is not more than 0.1 and pLNnH:LNnT is not more than 0.03, is obtainable, which mixture can be advantageously used for selectively crystallizing out LNnT. A mixture in which at least one of the ratios is higher than that defined above is unsuitable mixture for selective crystallization of LNnT.

The charcoal treatment can be conducted, e.g. by adding charcoal powder to the aqueous solution of carbohydrates under stirring, filtering off the charcoal, re-suspending in aqueous ethanol under stirring and separating the charcoal by filtration. In higher scale purification, the aqueous solution of carbohydrates after UF, NF or ion exchange treatment is preferably loaded to a column packed with charcoal, which may be a granulated charcoal or may optionally be mixed with celite, then the column is washed with the required eluent. The fraction containing LNT, LNTri II, pLNH II and lactose (if present), or LNnT, LNTri II, pLNnH and lactose (if present), is collected. Residual ethanol may be removed from the fraction, if necessary, by e.g. evaporation, to give an aqueous solution of LNT, LNTri II, pLNH II and lactose (if still present), or LNnT, LNTri II, pLNnH and lactose (if present).

A fifth (and optional) separation step may be a chromatography on a neutral solid phase, advantageously a reversed-phase chromatography. An aqueous solution comprising LNT, LNTri II, pLNH II and optionally lactose, or LNnT, LNTri II, pLNnH and optionally lactose, obtained in the fermentation process and/or after any of the separation steps disclosed above may contain small amounts of other soluble hydrophobic impurities which should be removed. The hydrophobic impurities are adsorbed and consequently retained, due to hydrophobic interactions with the hydrophobic ligands, such as alkyl or aryl side chains, of the gel matrix (resin) of the stationary neutral solid phase, while the more hydrophilic mixture of LNT, LNTri II, pLNH II and optionally lactose, or LNnT, LNTri II, pLNnH and optionally lactose, do not bind onto that solid medium and therefore can be eluted with an aqueous medium, preferably water, used as the mobile phase. During this fifth separation step, the weight ratios of LNT to LNTri II, to pLNH II and to lactose (if present), or LNnT, LNTri II, pLNnH and lactose (if present), do not change substantially.

The reversed-phase chromatography can be carried out in a conventional manner. Preferably, a hydrophobic chromatographic medium is used that is selected from the group consisting of: reversed-phase silicas and organic polymers, especially copolymers of styrene or divinylbenzene and methacrylate polymer. The silicas are preferably derivatized with straight chain alkyl hydrocarbons ranging in length from C1 to C18 (C1, C4, C5 C8 and C18 being the most common) or other hydrophobic ligands (for example phenyl or cyano).

To the aqueous medium used as the mobile phase in the reversed-phase chromatography an organic solvent may be added to alter its polarity, thereby to enhance the separation of oligosaccharides from more hydrophobic substances. Many organic solvents, preferably solvents miscible with water, can be used for this purpose, like lower alkanols, such as methanol, ethanol and isopropanol, or acetonitrile, or tetrahydrofuran, or acetone.

The reversed-phase chromatography can otherwise be carried out in a conventional manner, e.g. batch-wise or continuously. The purification can be easily done by using a conventional chromatographic column or container of laboratory or industrial scale, in which the hydrophobic chromatographic medium can be either packed or suspended (e.g. as beads).

Yet in one embodiment of the chromatography on a neutral solid phase, a gel filtration chromatography may be applied, when the pLNH II:LNT ratio higher than 0.05 in the mixture of LNT, LNTri II, pLNH II and lactose obtained in the fermentation process and/or after any of the separation steps disclosed above, in order to reduce it to 0.05 or below. The method is based on the separation of the hexasaccharide pLNH II by size from the lower oligosaccharides lactose, LNTri II and LNT. The weight ratios of LNTri II and lactose to LNT do not change substantially. Accordingly, by applying the above chromatography on an HMO mixture comprising or consisting of LNT, LNTri II, pLNH II and lactose wherein the weight ratios of lactose, LNTri II and pLNH II relative to LNT in the mixture are:

lactose:LNT is 0 to 0.2, LNTri II:LNT is not more than 0.15 and pLNH II:LNT is more than 0.05, an HMO mixture comprising or consisting of LNT, LNTri II, pLNH II and lactose wherein the weight ratios of lactose, LNTri II and pLNH II relative to LNT in the mixture are:

lactose:LNT=0 to 0.2, LNTri II:LNT is not more than 0.15 and pLNH II:LNT is not more than 0.05, is obtainable, which mixture can be advantageously used for selectively crystallizing out LNT.

Yet in one embodiment of the chromatography on a neutral solid phase, a gel filtration chromatography may be applied, when the pLNnH:LNnT ratio higher than 0.03 in the mixture of LNnT, LNTri II, pLNnH and lactose obtained in the fermentation process and/or after any of the separation steps disclosed above, in order to reduce it to 0.03 or below. The method is based on the separation of the hexasaccharide pLNnH by size from the lower oligosaccharides lactose, LNTri II and LNnT. The weight ratios of LNTri II and lactose to LNnT do not change substantially. Accordingly, by applying the above chromatography on an HMO mixture comprising or consisting of LNnT, LNTri II, pLNnH and lactose wherein the weight ratios of lactose, LNTri II and pLNnH relative to LNnT in the mixture are:

lactose:LNnT is 0 to 0.2, LNTri II:LNnT is not more than 0.1 and pLNnH:LNnT is more than 0.03, an HMO mixture comprising or consisting of LNnT, LNTri II, pLNnH and lactose wherein the weight ratios of lactose, LNTri II and pLNnH relative to LNnT in the mixture are:

lactose:LNnT=0 to 0.2, LNTri II:LNnT is not more than 0.1 and pLNnH:LNnT is not more than 0.03, is obtainable, which mixture can be advantageously used for selectively crystallizing out LNnT.

The gel filtration chromatography is conducted in a conventional manner.

If the mixture of LNT, LNTri II, pLNH II and lactose obtained in the fermentation process and/or after any of the separation steps disclosed above has a lactose: LNT ratio more than 0.2 but less than 0.8 and a pLNH II:LNT ratio more than 0.05, both active charcoal treatment and gel filtration, as disclosed above, should be applied in order to get an HMO mixture comprising or consisting of LNT, LNTri II, pLNH II and lactose which is suitable for crystallizing LNT.

If the mixture of LNnT, LNTri II, pLNnH and lactose obtained in the fermentation process and/or after any of the separation steps disclosed above has a lactose:LNnT ratio more than 0.2 but less than 0.8 and a pLNnH:LNnT ratio more than 0.03, both active charcoal treatment and gel filtration, as disclosed above, should be applied in order to get an HMO mixture comprising or consisting of LNnT, LNTri II, pLNnH and lactose which is suitable for crystallizing LNnT.

Third Aspect of the Invention

The third aspect of the invention relates to a method for the selective crystallization of:

either LNT wherein the crystallization is carried out from a mixture comprising LNT, LNTri II, pLNH II and optionally lactose, and having weight ratios of lactose, LNTri II and pLNH II relative to LNT:

lactose:LNT=0 to 0.2, LNTri II:LNT is not more than 0.15 and pLNH II:LNT is not more than 0.05, using one or more monohydroxy $C_1$-$C_4$ alcohol(s) as antisolvent(s), or LNnT wherein the crystallization is carried out from a mixture comprising LNnT, LNTri II, pLNnH and optionally lactose, and having weight ratios of lactose, LNTri II and pLNnH relative to LNnT:

lactose:LNnT=0 to 0.2, LNTri II:LNnT is not more than 0.1 and pLNnH:LNnT is not more than 0.03, using one or more monohydroxy $C_1$-$C_4$ alcohol(s) and/or acetone as antisolvent(s).

The crystallization is typically a solvent-antisolvent crystallization, in which the above HMO mixture is taken as its aqueous solution. The antisolvent is preferably methanol.

If the crystallization of LNnT is carried out with a reverse order addition (that is the aqueous oligosaccharide solution is added to the antisolvent), the antisolvent is preferably acetone, and the LNnT crystallized so is preferably its polymorph disclosed in EP-A-1405856. If the crystallization is conducted with a normal order addition (that is the antisolvent is added to the aqueous solution of the oligosaccharide mixture), the antisolvent is preferably a monohydroxy $C_1$-$C_4$ alcohol, advantageously methanol, and the LNnT crystallized so is preferably its polymorph disclosed in WO 2011/100980.

Fourth Aspect of the Invention

The HMO mixtures of this invention containing, preferably consisting essentially of LNT, LNTri II, pLNH II and optionally lactose, or LNnT, LNTri II, pLNnH and optionally lactose, are anti-infective compositions that can be used for treating and/or preventing viral and/or bacterial, intestinal infections through specific modulation of the gastrointestinal microbiota, modulation of intestinal binding of viruses and pathogenic bacteria, and improvement of intestinal barrier function and immune function. In particular, the mixtures increase *Bifidobacterium* abundance, especially members of the *Bifidobacterium adolescentis* phylogenetic group, especially *Bifidobacterium adolescentis* and/or *Bifidobacterium pseudocatenulatum* and, after about 14 days, *Bifidobacterium longum* and/or *Bifidobacterium bifidum*, in the intestinal microbiota. The mixtures may also reduce the abundance of Firmicutes, especially Clostridia, and pathogenic bacteria. Further, each mixture acts as a decoy receptor and binds to rotaviruses to prevent the rotaviruses from adhering to intestinal cells. These properties, coupled with an improvement in intestinal barrier function and immune function, make the mixtures suitable for preventing and treating viral and/or bacterial infections. The mixtures also reduce the abundance of *Ruminococcus gnavus* which has been associated with intestinal diseases such as inflammatory bowel disease and irritable bowel syndrome. This, coupled with an improvement in intestinal barrier function and immune function, makes the mixtures suitable for preventing and treating conditions such as inflammatory bowel disease, irritable bowel syndrome, and other conditions associated with inflammation and impaired barrier function.

The HMO mixtures of this invention containing, preferably consisting essentially of LNT, LNTri II, pLNH II and optionally lactose, or LNnT, LNTri II, pLNnH and optionally lactose, can also be used for preventing and/or treating viral and/or bacterial infections of the respiratory tract. In this regard, the mixtures impact host defences including modulation of the immune system leading to inhibition of respiratory pathogen colonization.

The anti-infective compositions of this invention can be pharmaceutical compositions. Each pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to a patient. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The anti-infective compositions of this invention can be administered orally, e.g. as a tablet, capsule, or pellet containing a predetermined amount of the first mixture, or as a powder or granules containing a predetermined concentration of the first mixture or a gel, paste, solution, suspension, emulsion, syrup, bolus, electuary, or slurry, in an aqueous or non-aqueous liquid, containing a predetermined concentration of the first mixture. Orally administered compositions can include binders, lubricants, inert diluents, flavouring agents, and humectants. Orally administered corn positions such as tablets can optionally be coated and can be formulated so as to provide sustained, delayed or controlled release of the first mixture therein.

The anti-infective compositions of this invention can also be administered by rectal suppository, aerosol tube, nasogastric tube or direct infusion into the GI tract or stomach.

Anti-infective pharmaceutical compositions of this invention can also include therapeutic agents such as antiviral agents, antibiotics, probiotics, analgesics, and anti-inflammatory agents. The proper dosage of these compositions for a patient can be determined in a conventional manner, based upon factors such as the patient's immune status, body weight and age. In some cases, the dosage will be at a concentration similar to that found for ingredients of the mixtures in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by methods known to those skilled in the art.

The anti-infective compositions of this invention can also be added to nutritional compositions. For example, they can be added to a rehydration solution, or a dietary maintenance or supplement for elderly individuals or immunocompromised individuals. Macronutrients such as edible fats, carbohydrates and proteins can also be included in such anti-infective compositions. Edible fats include, for example, coconut oil, soy oil and monoglycerides and diglycerides. Carbohydrates include, for example, glucose, edible lactose and hydrolysed cornstarch. Proteins include, for example, soy protein, whey, and skim milk. Vitamins and minerals (e. g. calcium, phosphorus, potassium, sodium, chloride, magnesium, manganese, iron, copper, zinc, selenium, iodine, and Vitamins A, E, D, C, and B complex) can also be included in such anti-infective compositions.

Fifth Aspect of the Invention

A fifth aspect of this invention relates to a method of modulating the gastrointestinal microbiota of a human to increase *Bifidobacterium* abundance. The method comprises administering, to the human, a mixture of LNT, pLNH II and LNTri II, or a mixture of LNnT, pLNnH and LNTri II, advantageously the synthetic HMO mixture of the first aspect of this invention, or a nutritional or pharmaceutical composition comprising thereof.

Sixth Aspect of the Invention

A sixth aspect of this invention relates to a method of preventing or treating viral and/or bacterial infections in a human, especially intestinal infections and infections of the respiratory tract. The method comprises administering, to the human, a mixture of LNT, pLNH II and LNTri II, or a mixture of LNnT, pLNnH and LNTri II, advantageously the synthetic HMO mixture of the first aspect of this invention or a nutritional or pharmaceutical composition comprising thereof.

Whilst the invention has been described with reference to a preferred embodiment, it will be appreciated that various modifications are possible within the scope of the invention.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

EXAMPLES

Example 1

Making a mixture consisting essentially of LNT, LNTri II, pLNH II and lactose, or LNnT, LNTri II, pLNnH and lactose Bacterial strain:

A strain is constructed from *Escherichia coli* K12 strain DH1, obtained from the Deutsche Sammlung von Mikroorganismen (reference DSM 5346). The following genes are deleted: *lacZ, nanKETA, lacA, melA, wcaJ* and mdoH by inserting a Plac promoter, while maintaining genes involved in the UDP-GlcNAc and UDP-Gal biosynthesis. The strain contains a plasmid comprising a β-1,3-N-acetylglucosaminyl transferase (IgtA) and antibiotic marker (plasmid 1), and a plasmid comprising a β-1,3-galactosyl transferase with antibiotic marker (plasmid 2) [for producing LNT], or pBBR3-IgtA-tet plasmid carrying *N. meningitidis IgtA* gene for β-1,3-N-acetylglucosaminyl transferase and the tetracycline resistant gene, and a pBS-galT-amp plasmid carrying *Helicobacter pylori galT* gene for β-1-4-galactosyl transferase and the ampicillin resistant gene [for producing LNnT].

Fermentation Procedure:

Glucose, glycerol and lactose are each sterilized at 120° C. Isopropyl thio-β-D-galactopyranoside (IPTG) was filter sterilized.

The fermentation is carried out in a 3 l fermenter containing ≈0.9 l of aqueous mineral culture medium (Samain et al. *J. Biotechnol.* 72, 33 (1999). The temperature is kept at 33° C. and the pH regulated at 6.8 with 28% $NH_4OH$. The inoculum of the strain is in an LB medium (20 ml) supplemented with ampicillin and tetracycline. The exponential growth phase starts with the inoculation and stops when the glucose carbon source, initially added to the aqueous culture medium, is exhausted. A lactose solution (70 g of lactose/500 ml of water) is then added to the aqueous culture medium before starting the feeding with a 500 g/l solution, 4.5 g/h of glycerol as the carbon source. 1-2 ml of a 50 mg/ml solution of isopropyl thio-β-D-galactopyranoside (IPTG) as an inducer, is also added to the aqueous culture medium. The glycerol-fed fermentation lasts for about 90 hours and produces a final aqueous culture medium containing:

a) [for the LNT producing strain] LNT, LNTri II, pLNH II and lactose in the following ratios:
   lactose:LNT=0.15 to 0.20
   LNTri II:LNT=0.05 to 0.12
   pLNH II:LNT=0.005 to 0.03; or b) [for the LNnT producing strain] LNnT, LNTri II, pLNnH and lactose in the following ratios:
   lactose:LNnT=0.43 to 0.72
   LNTri II:LNnT=0.03 to 0.05
   pLNnH:LNnT=0.19 to 0.20
   and having an LNnT titre of 45 g/l.

Purification Procedure:

Purification of the final aqueous culture medium from each batch is carried out by the following sequential steps:

i) centrifugation of the culture medium to separate the *E. coli* cells, suspended particulates and contaminants, insoluble materials and debris from the remaining culture medium;

ii) washing the separated cells with warm water and then adding the wash water to the remaining culture medium;

iii) ultrafiltration of the remaining culture medium with a ceramic membrane having a pore size of 50 kDA MWCO and then another ultrafiltration of the culture medium with a ceramic membrane having a pore size of 1 kDA MWCO to remove cell proteins, peptides, amino acids, RNA and DNA, endotoxins and glycolipids;

iv) treatment of the culture medium with a strongly acidic, cationic ion exchange, DOWEX 50 WX 12, and a weakly basic, anionic ion exchange ion exchange resin, DOWEX 66, to remove minerals, salts and other charged molecules, as well as amino acids, remaining proteins, DNA and colorizing/caramel bodies; and then v) decolorization of the culture medium with activated charcoal.

The resulting culture mediums are aqueous second HMO mixtures of this invention, which consist essentially of a) lactose, LNTri II, LNT and pLNH II and in which the ratios of lactose, LNTri II, LNT and pLNH II are as follows:
   lactose:LNT=0.15 to 0.20
   LNTri II:LNT=0.05 to 0.12
   pLNH II:LNT=0.005 to 0.03; or b) lactose, LNTri II, LNnT and pLNnH and in which the ratios of lactose, LNTri II, LNnT and pLNnH are as follows:
   lactose:LNnT=0.43 to 0.72
   LNTri II:LNnT=0.03 to 0.05
   pLNnH:LNnT=0.18 to 0.20, respectively.

Example 2

Making a dry mixture consisting essentially of LNT, LNTri II, pLNH II and lactose or LNnT, LNTri II, pLNnH and lactose The aqueous mixture of LNT, LNTri II, pLNH II and lactose or that of LNnT, LNTri II, pLNnH and lactose from Example 1 is subjected to nanofiltration with a membrane of 200 Da to remove most of the remaining water. The resulting wet second HMO mixtures of this invention of LNTri II, LNT, pLNH II and lactose or that of LNTri II, LNnT, pLNnH and lactose is then subjected to further drying by heating to remove substantially all the remaining water; the weight ratios in the resulting dry mixture are as follows:
   lactose:LNT=0.15 to 0.20
   LNTri II:LNT=0.05 to 0.12
   pLNH II:LNT=0.005 to 0.03; or
   lactose:LNnT=0.43 to 0.72
   LNTri II:LNnT=0.03 to 0.05
   pLNnH:LNnT=0.18 to 0.19.

Example 3

Thirty male and female patients are recruited to participate in the study. After a screening visit and run-in period of 1-2 weeks, the patients are selected and randomized into three groups, each of 10 patients. Two groups are administered the treatment product and one group the placebo product for 8 weeks. The treatment product contains a) 5 grams of a combination of LNT, LNTri II and pLNH II or b) 5 grams of a combination of LNnT, LNTri II and pLNnH, while the placebo product contains 2 grams of glucose. All products are in powder form in a unit dosage container.

The patients are eligible to participate if they are at least 18 years of age. All recruited patients are able and willing to understand and comply with the study procedures. Patients are excluded if: they have participated in a clinical study one month prior to screening visit;

they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 2 months prior to the study; consumed antibiotic drugs 3 months prior to the study; consumed on a regular basis any medication that might interfere with symptom evaluation 2 weeks prior to the study; and pregnant or lactating.

At the screening visit, medical history and concomitant medication is registered and a blood sample for safety analyses is collected. A faecal sample kit is distributed. Patients are instructed to keep the collected faecal samples in the freezer until the next visit.

At the second visit, eligibility criteria are checked and eligible subjects are randomised to the three arms in the trial. The faecal samples are collected and equipment for new samples are distributed. Patients are familiarised with an interactive internet enabled system which records data daily and are provided with either treatment or placebo products. Subjects are reminded not to change their usual diet during the study. Blood samples are collected for biomarker studies. The faecal samples are stored at −80° C. until analysis. Faecal samples are subjected to 16S rRNA sequencing analysis.

The study runs for 8 weeks with the patients consuming either a placebo or a treatment product daily. Patients are instructed to consume the products in the morning with breakfast. Compliance is monitored through the interactive internet enabled system. The patients also use the system to record:

Bristol Stool Form Scale (BSFS) information,
symptom information such as abdominal pain, abdominal discomfort, abdominal cramping, abdominal bloating, and abdominal fullness,
additional Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of the study, each patient has an exit visit with the medical team. Faecal samples and blood samples are collected and analysed as before.

The faecal analysis indicates that the treatment patients have increased abundance of *Bifidobacterium*.

Example 4

Thirty 5-day old Sprague-Dawley rats are individually housed to avoid contamination between rats and provided with irradiated food and water. The rats are separated into 3 groups of 10 rats: two treatment groups and a control group.

A mixture of LNT, LNTri II and pLNH II and a mixture of LNnT, LNTri II and pLNnH is added to the drinking water of each treatment group, respectively, at a total concentration of 40 mg/ml. The water of the control group is not altered (day 0). Fresh water is administered daily and all rats have free access to the drinking water. The rats are fed a rodent chow and are given fresh chow daily.

Two days after administration of the mixture (day 2), the rats of all groups are infected by means of oral gavage with an encapsulated *S. pneumoniae* strain.

After 24 hours, the rats are subjected to nasal washing using a saline solution. The solution is recovered and the number of viable bacteria is obtained by counting colonies on agar plates. The rats are monitored for 1 week and are then euthanized (day 10). After euthanization, the lungs are harvested. Lung tissue is finely minced in 10 ml of PBS and subsequently homogenized (2 minutes/sample) with a Stomacher. The tissue homogenates are serially diluted and cultured on selective Strep Agar for 48 hours and colony-forming units (cfu) are determined.

In the treated rats, *S. pneumoniae* colonisation of the lungs is reduced compared to the control rats. Similarly, the quantity of viable *S. pneumonia* recovered in the nasal wash of the treated rats is reduced compared to the control rats.

The invention claimed is:

1. A process for obtaining a mixture of LNTri II, LNT and pLNH II, or LNTri II, LNnT and pLNnH, and optionally lactose, comprising the steps of:
   a) providing a genetically modified cell comprising:
      a first recombinant gene encoding an N-acetyl-glucosaminyl transferase enzyme which is able to transfer a GlcNAc from a UDP-GlcNAc to lactose in said cell to form LNTri II,
      a second recombinant gene encoding a galactosyl transferase enzyme which is able to transfer a galactosyl residue from a UDP-Gal to LNTri II in said cell to form a component A which is LNT or LNnT, and
      genes encoding biosynthetic pathways in said cell to said UDP-GlcNAc and to said UDP-Gal,
   b) culturing said cell in a culture medium containing lactose, thereby inducing:
      internalization of said lactose into said cell, preferably via an active transport mechanism, and
      formation of LNTri II, a component A and a component B, wherein component B is pLNH II when component A is LNT, or component B is pLNnH when component A is LNnT, in said cell, and
   c) optionally, continuing the culturing according to step b) until no lactose is left, and
   d) separating and isolating a mixture of LNTri II, component A, component B and optionally lactose from the culture medium.

2. The process of claim 1, wherein in step d) said culture medium is treated by centrifugation, ultrafiltration, ion exchange and then decolorization.

3. The process of claim 2, wherein after step d), said culture medium is treated by nanofiltration to remove water from said culture medium.

4. A method of modulating the microbiota of a human to increase *Bifidobacterium* abundance, the method comprising administering, to the human, a mixture consisting essentially of:
   LNTri II,
   a component A which is LNT or LNnT,
   a component B which is:
      pLNH II when component A is LNT, or
      pLNnH when component A is LNnT
   and optionally, lactose.

5. A method of treating viral and/or bacterial infections in a human, the method comprising administering, to the human, a mixture consisting essentially of:
   LNTri II
   a component A which is LNT or LNnT,
   a component B which is:
      pLNH II when component A is LNT, or
      pLNnH when component A is LNnT
   and optionally, lactose.

6. A method for crystallizing LNnT comprising dissolving a mixture of LNnT, LNTri II, pLNnH, and optionally, lactose in water to form an aqueous solution,
  adding the aqueous solution to an antisolvent; or adding the antisolvent to the aqueous solution, and
  obtaining a crystalline form of LNnT,
  wherein the mixture prior to dissolution comprises the following weight ratios of lactose, LNTri II and pLNnH relative to LNnT:
    lactose:LNnT is 0 to 0.2,
    LNTri II:LNnT is not more than 0.1 and
    pLNnH:LNnT is not more than 0.03, and
  wherein the antisolvent is one or more monohydroxy $C_1$-$C_4$ alcohol(s) and/or acetone.

7. A method for crystallizing LNT comprising
  obtaining a mixture comprising LNT, LNTri II, pLNH II and optionally lactose, wherein the mixture comprises the following weight ratios of lactose, LNTri II and pLNH II relative to LNT:
    lactose:LNT is 0 to 0.2,
    LNTri II:LNT is not more than 0.15 and
    pLNH II:LNT is not more than 0.05; and
  using one or more monohydroxy $C_1$-$C_4$ alcohol(s) as antisolvent(s).

8. The process of claim 1, wherein the genetically modified cell is a bacterial cell.

9. The process of claim 8, wherein the bacterial cell is an *E. coli* cell.

10. The method of claim 4, wherein the mixture comprises LNTri II, LNnT, pLNnH and optionally lactose, and wherein the weight ratios of LNTri II, pLNnH and optionally lactose relative to LNnT are:
  LNTri II:LNnT is not more than 0.1;
  LNnH:LNnT is not more than 0.4; and
  lactose:LNnT is 0 to 0.8.

11. The method of claim 10, wherein the weight ratios of:
  pLNnH:LNnT is not more than 0.03; and
  lactose:LNnT is 0 to 0.2.

12. The method of claim 4, wherein the mixture comprises LNTri II, LNT, pLNH II and optionally lactose, wherein the weight ratios of LNTri II, pLNH II and optionally lactose relative to LNT are:
  LNTri II:LNT is not more than 0.2;
  pLNH II:LNT is not more than 0.05; and
  lactose:LNT is 0 to 0.6.

13. The method of claim 4, wherein the mixture essentially consists of LNTri II, LNnT, pLNnH and lactose, and wherein the weight ratios of lactose, LNTri II and pLNnH relative to LNnT are:
  lactose:LNnT is 0.2 to 0.8;
  LNTri II:LNnT is 0.01 to 0.05; and
  pLNnH:LNnT is 0.1 to 0.2.

14. The method of claim 4, wherein the mixture essentially consists of LNTri II, LNT, pLNH II and lactose, and wherein the weight ratios of lactose, LNTri II and pLNH II relative to LNT are:
  lactose:LNT is 0.15 to 0.20;
  LNTri II:LNT is 0.05 to 0.12; and
  pLNH II:LNT is 0.005 to 0.03.

15. The method of claim 5, wherein the mixture comprises LNTri II, LNnT, pLNnH and optionally lactose, and wherein the weight ratios of LNTri II, pLNnH and optionally lactose relative to LNnT are:
  LNTri II:LNnT is not more than 0.1;
  pLNnH:LNnT is not more than 0.4; and
  lactose:LNnT is 0 to 0.8.

16. The method of claim 15, wherein the weight ratios of:
  pLNnH:LNnT is not more than 0.03; and
  lactose:LNnT is 0 to 0.2.

17. The method of claim 5, wherein the mixture comprises LNTri II, LNT, pLNH II and optionally lactose, wherein the weight ratios of LNTri II, pLNH II and optionally lactose relative to LNT are:
  LNTri II:LNT is not more than 0.2;
  pLNH II:LNT is not more than 0.05; and
  lactose:LNT is 0 to 0.6.

18. The method of claim 5, wherein the mixture essentially consists of LNTri II, LNnT, pLNnH and lactose, and wherein the weight ratios of lactose, LNTri II and pLNnH relative to LNnT are:
  lactose:LNnT is 0.2 to 0.8;
  LNTri II:LNnT is 0.01 to 0.05; and
  pLNnH:LNnT is 0.1 to 0.2.

19. The method of claim 5, wherein the mixture essentially consists of LNTri II, LNT, pLNH II and lactose, and wherein the weight ratios of lactose, LNTri II and pLNH II relative to LNT are:
  lactose:LNT is 0.15 to 0.20;
  LNTri II:LNT is 0.05 to 0.12; and
  pLNH II:LNT is 0.005 to 0.03.

* * * * *